United States Patent
Miehlich et al.

(10) Patent No.: US 9,545,372 B2
(45) Date of Patent: Jan. 17, 2017

(54) ORAL AND DENTAL HYGIENE AND CLEANING AGENTS FOR REDUCING RE-STAINING OF TEETH

(71) Applicant: Henkel AG & Co. KGaA, Duesseldorf (DE)

(72) Inventors: Kristin Miehlich, Wuppertal (DE); Thomas Welss, Duesseldorf (DE); Daniela Arians, Essen (DE); Samantha Bidault, Bullion (FR)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/972,180

(22) Filed: Dec. 17, 2015

(65) Prior Publication Data

US 2016/0101035 A1 Apr. 14, 2016

Related U.S. Application Data

(63) Continuation of application No. PCT/EP2014/051682, filed on Jan. 29, 2014.

(30) Foreign Application Priority Data

Jun. 19, 2013 (DE) ........................ 10 2013 211 519

(51) Int. Cl.
| | | |
|---|---|---|
| *A61K 8/81* | (2006.01) | |
| *A61K 8/25* | (2006.01) | |
| *A61K 8/73* | (2006.01) | |
| *A61Q 11/00* | (2006.01) | |

(52) U.S. Cl.
CPC . *A61K 8/81* (2013.01); *A61K 8/25* (2013.01); *A61K 8/736* (2013.01); *A61K 8/8164* (2013.01); *A61Q 11/00* (2013.01); *A61K 2800/20* (2013.01); *A61K 2800/594* (2013.01)

(58) Field of Classification Search
USPC ........................................... 514/55
See application file for complete search history.

(56) References Cited

U.S. PATENT DOCUMENTS

| | | | | |
|---|---|---|---|---|
| 6,638,918 | B2 * | 10/2003 | Davison ................... | A61K 8/02 514/55 |
| 9,308,158 | B2 * | 4/2016 | Chandrasekaran ...... | A61K 8/26 |

FOREIGN PATENT DOCUMENTS

| | | |
|---|---|---|
| DE | 102010062611 A1 | 6/2012 |
| EP | 2556817 A2 | 2/2013 |
| WO | 03/042251 A1 | 5/2003 |

OTHER PUBLICATIONS

PCT International Search Report (PCT/EP2014/051682) dated Jul. 5, 2014.
Sano et al., "Effect of Chitosan Rinsing on Reduction of Dental Plaque Formation", XP055015488, Bulletin of Tokyo Dental College, vol. 44, No. 1, pp. 9-16, 2003.
Lynch, "Calcium Glycerophosphate and Caries: A Review of the Literature", XP009177764, International Dental Journal, VOl. 54, No. 5, pp. 310-314, 2004.
Ganss et al., "Toothpaste and Erosion", XP009177755, Toothpastes, Karger Medical and Scientific Publishers, vol. 23, pp. 88-99, 2013.

* cited by examiner

*Primary Examiner* — Walter Webb
(74) *Attorney, Agent, or Firm* — P. Scott Smith

(57) ABSTRACT

The invention relates to oral and dental hygiene and cleaning agents for reducing restaining of teeth.

20 Claims, No Drawings

ORAL AND DENTAL HYGIENE AND CLEANING AGENTS FOR REDUCING RE-STAINING OF TEETH

FIELD OF THE INVENTION

The present invention generally relates to oral and dental hygiene agents with an active substance combination for the gentle and effective cleaning of teeth.

BACKGROUND OF THE INVENTION

Dental cleaning agents are on the market in various forms and serve primarily to clean the tooth surface and to prevent tooth and gum diseases. They typically include a combination of polishing agents, humectants, surfactants, binders, flavoring agents, and fluoride-containing and antimicrobial active substances. Apart from tooth powders, which play a minor role because of their increased abrasiveness, dental cleaning agents are offered primarily in paste, cream, and translucent or transparent gel form. Liquid dental creams and mouthwashes have also become increasingly important in recent years.

Many people desire white teeth and perceive dark or stained teeth as cosmetically unacceptable. The maintenance of the natural tooth color is not always successful, however, despite regular dental hygiene. Dietary habits or smoking can lead to tooth discoloration. Likewise, the colonization of the tooth surface by bacteria (plaque) leads to discoloration.

A number of technical solutions for plaque removal or whitening of teeth were developed. Peroxide is used primarily for whitening/bleaching. Peroxide is used in high concentrations in professional bleaching products, whereas use in cosmetic products for oral and dental hygiene is limited to 0.1% peroxide. Peroxide in this concentration has only a limited whitening effect and often does not eliminate tooth discoloration to the desired extent.

Another option for whitening teeth is the effective removal of plaque, which makes teeth appear darker. This method of tooth whitening is also described as "natural whitening." A high cleaning performance is best achieved by cleaning substances, for example, silica, alumina, or calcium carbonate in combination with a surfactant. Unfortunately, dental creams with an effective system of one or more cleaning substances often also have a high abrasiveness, and therefore often lead to a certain, albeit very low abrasion of the tooth surface. This can be particularly disadvantageous, when the tooth enamel is already thin, as is the case in people with sensitive teeth. Exposed tooth necks also occur often in individuals with sensitive teeth, therefore the portions of the tooth in the immediate vicinity of the gum where no enamel is present as a protective layer and the underlying dentin is exposed.

Moreover, immediately after teeth cleaning, a protein layer (pellicle) forms on the tooth material on which layer plaque builds up or discolorations accumulate.

There is a need, therefore, for toothpastes that achieve an effective cleaning and whitening but at the same time produce a long-term effect, i.e., prevent or reduce as long as possible the formation of new plaque and thereby new discolorations.

The object of the present invention was to provide preparations for oral and dental hygiene and cleaning that achieve effective cleaning and whitening and thereby prevent or reduce new discolorations as long as possible.

It was now found surprisingly that a combination of two polymers with certain abrasive substances has the result that stains (e.g., from food, particularly tea stains) are less evident. The gentle cleaning by such a combination is supplemented with a long-term effect against restaining.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An oral and dental hygiene and cleaning agent, including, based on its weight, 0.001 to 5% by weight of copolymer(s), comprising at least one structural unit of formula (A1) and at least one structural unit of formula (A2)

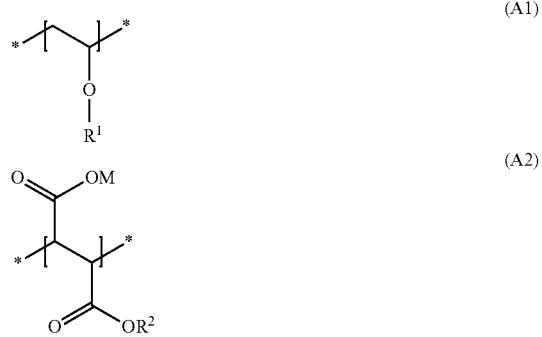

where $R^1$ stands for a ($C_1$ to $C_{18}$) alkyl group, $R^2$ stands for a ($C_1$ to $C_6$) alkyl group, M stands for a hydrogen atom or an equivalent of a mono- or polyvalent cation; 0.001 to 5% by weight of polymer(s) from the group comprising chitosan and chitosan derivatives; and 1 to 20% by weight of precipitated silicic acid(s) with a specific surface of ≤60 m²/g according to ISO 5794-1, Annex D.

Use of oral and dental hygiene and cleaning agents, including, based on their weight, 01 to 5% by weight of copolymer(s), comprising at least one structural unit of formula (A1) and at least one structural unit of formula (A2)

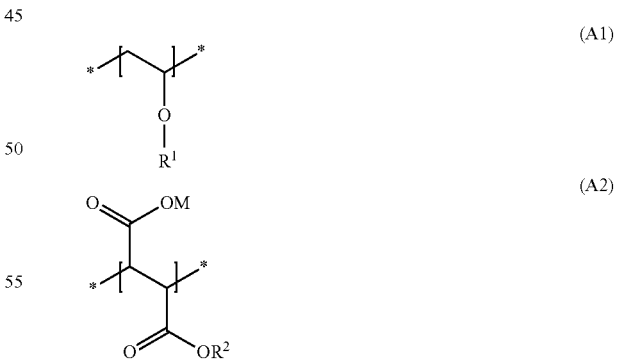

where $R^1$ stands for a ($C_1$ to $C_{18}$) alkyl group, $R^2$ stands for a ($C_1$ to $C_6$) alkyl group, M stands for a hydrogen atom or an equivalent of a mono- or polyvalent cation; 0.001 to 5% by weight of polymer(s) from the group comprising chitosan and chitosan derivatives; and 1 to 20% by weight of precipitated silicic acid(s) with a specific surface of ≤60 m²/g according to ISO 5794-1, Annex D to reduce the restaining of teeth.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject of the invention comprises oral and dental hygiene and cleaning agents, including, based on their weight, a) 0.001 to 5% by weight of copolymer(s), comprising at least one structural unit of formula (A1) and at least one structural unit of formula (A2)

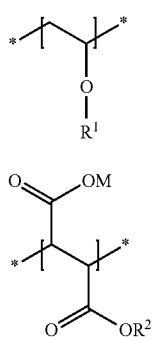

(A1)

(A2)

where $R^1$ stands for a ($C_1$ to $C_{18}$) alkyl group, $R^2$ stands for a ($C_1$ to $C_6$) alkyl group, M stands for a hydrogen atom or an equivalent of a mono- or polyvalent cation, b) 0.001 to 5% by weight of polymer(s) from the group comprising chitosan and chitosan derivatives, c) 1 to 20% by weight of precipitated silicic acid(s) with a specific surface of ≤60 m²/g according to ISO 5794-1, Annex D.

Oral and dental hygiene agents and oral and dental cleaning agents within the meaning of the invention are oral and tooth powders, oral pastes and toothpastes, liquid oral and dental creams, oral and dental rinses, and oral and tooth gels. Suitable with preference are toothpastes and liquid tooth cleaning agents. To this end, the oral and dental hygiene and cleaning agents can be, e.g., in the form of toothpastes, liquid dental creams, tooth powders, mouthwashes, or optionally as a gum base, e.g., as chewing gum. Preferably, however, they are present as more or less flowable or plastic toothpastes, as they are used for cleaning teeth with use of a toothbrush. Another especially preferred embodiment of the present invention comprises mouth rinse solutions and mouthwashes, which are used for rinsing the oral cavity.

The compositions of the invention include as the first essential ingredient, based on their weight, 0.001 to 5% by weight of copolymer(s), comprising at least one structural unit of formula (A1) and at least one structural unit of formula (A2)

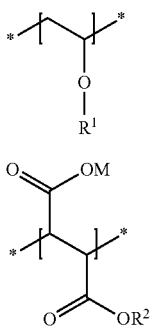

(A1)

(A2)

where $R^1$ stands for a ($C_1$ to $C_{18}$) alkyl group, $R^2$ stands for a ($C_1$ to $C_6$) alkyl group, M stands for a hydrogen atom or an equivalent of a mono- or polyvalent cation.

According to the above formulas and all following formulas, a chemical bond labeled with the symbol * stands for a free valence of the corresponding structural fragment.

Examples of ($C_1$ to $C_4$) alkyl groups of the invention are methyl, ethyl, propyl, isopropyl, butyl, sec-butyl, isobutyl, and tert-butyl.

Examples of ($C_8$ to $C_{30}$) alkyl groups of the invention are octyl (capryl), decyl (caprinyl), dodecyl (lauryl), tetradecyl (myristyl), hexadecyl (cetyl), octadecyl (stearyl), eicosyl (arachyl), and docosyl (behenyl).

It is preferred according to the invention, if the agents of the invention include as component (b) at least one polymer, selected from at least one polymer of the group with polymers with the INCI nomenclature Butyl Ester of PVM/MA Copolymer, Isopropyl Ester of PVM/MA Copolymer, Ethyl Ester of PVM/MA Copolymer.

Suitable polymers of component a) of the agent of the invention are available, for example, under the trade name Gantrez® ES 425 (copolymer of methyl vinyl ether and the butyl half ester of maleic acid; 50% by weight of active substance in ethanol; INCI name: Butyl Ester of PVM/MA Copolymer (Ashland)), Gantrez® ES 435 (copolymer of methyl vinyl ether and the butyl half ester of maleic acid; 50% by weight of active substance in isopropanol; INCI name: Butyl Ester of PVM/MA Copolymer (Ashland)), Gantrez® ES 3351 (copolymer of methyl vinyl ether and the isopropyl half ester of maleic acid; 50% by weight of active substance in isopropanol; INCI name: Butyl Ester of PVM/MA Copolymer (Ashland)), and Gantrez® ES 225 (copolymer of methyl vinyl ether and the ethyl half ester of maleic acid; 50% by weight of active substance in ethanol) INCI name: Ethyl Ester of PVM/MA Copolymer (Ashland)).

Very especially preferred polymers a) have at least one structural unit of formula (A1) and at least one structural unit of formula (A2), in which $R^1=R^2=M=-H$; i.e., copolymers of methyl vinyl ether and maleic acid can be used especially preferably according to the invention. Such copolymers are sold, for example, under the trade name Gantrez® S 97 BF (copolymer of methyl vinyl ether and maleic acid (Ashland)).

Especially preferred oral and dental hygiene and cleaning agents of the invention are characterized in that they include, based on their weight, 0.002 to 4% by weight, preferably 0.003 to 3% by weight, particularly preferably 0.004 to 2% by weight, exceedingly preferably 0.005 to 1% by weight, and in particular 0.01 to 0.5% by weight of copolymer(s) of maleic acid and methyl vinyl ether.

It turned out that copolymers a) of a specific molar mass range are especially effective in the combination of the invention. Especially preferred oral and dental hygiene and cleaning agents of the invention are therefore characterized in that the copolymer(s), comprising at least one structural unit of formula (A1) and at least one structural unit of formula (A2), has/have molar masses of 500,000 to 5,000,000 daltons, preferably of 600,000 to 4,000,000 daltons, more preferably of 700,000 to 3,000,000, even more preferably of 800,000 to 2,000,000 daltons, and in particular of 900,000 to 1,500,000 daltons.

Very especially preferable again is the use of copolymers of methyl vinyl ether and maleic acid, so that particularly preferred oral and dental hygiene and cleaning agents are characterized in that they include, based on their weight, 0.002 to 4% by weight, preferably 0.003 to 3% by weight, particularly preferably 0.004 to 2% by weight, exceedingly preferably 0.005 to 1% by weight, and in particular 0.01 to 0.5% by weight of copolymer(s) of methyl vinyl ether and maleic acid, which has/have molar masses of 500,000 to 5,000,000 daltons, preferably of 600,000 to 4,000,000 daltons, more preferably of 700,000 to 3,000,000, even more preferably of 800,000 to 2,000,000 daltons, and in particular of 900,000 to 1,500,000 daltons.

The agents of the invention include as the second essential ingredient 0.001 to 5% by weight of polymer(s) from the group comprising chitosan and/or at least one of its derivative(s).

Chitosan is the deacetylation product of chitin, whereby there is no defined transition between chitosan and chitin. Within the scope of the present invention, the term chitosan is used when the degree of chitin deacetylation is at least 20%. Preferred agents of the invention include chitosans (or derivatives thereof), whose degree of deacetylation is >30%, in particular >40-50%. Preferred further are chitosans and derivatives thereof which are soluble in organic acids.

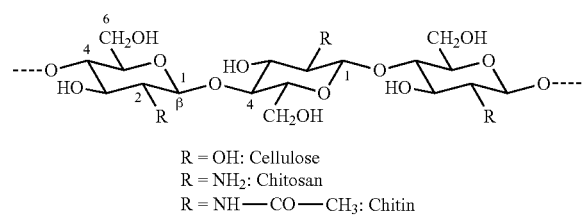

R = OH: Cellulose
R = NH$_2$: Chitosan
R = NH—CO—CH$_3$: Chitin

Preferred chitosans or derivatives thereof, used according to the invention, have molar masses of 100,000 to 500,000 daltons. Chitosan consists of chains of beta-1,4-glycosidically linked N-acetyl-D-glucosamine (NAG) residues.

Preferred oral and dental hygiene and cleaning agents of the invention are characterized in that they include, based on their weight, 0.002 to 4% by weight, preferably 0.003 to 3% by weight, particularly preferably 0.004 to 2% by weight, exceedingly preferably 0.005 to 1% by weight, and in particular 0.01 to 0.5% by weight of polymer(s) from the group comprising chitosan and chitosan derivatives.

Preferably, the chitosans or derivatives thereof used in the agents of the invention are water-soluble. Preferred agents of the invention are characterized in that they include chitosan derivative(s) that have a water solubility in distilled water above of 1 g/L (20° C., 1013 mbar).

Chitosan derivatives to be used with preference are derivatized at the amino group. Especially preferred chitosan derivatives have an acid residue, preferably the residue of an organic acid, bound to the nitrogen atom of the amino group. Especially preferred chitosan derivatives have at least one acid residue of the following acids bound to the nitrogen atom of the amino group: formic acid, acetic acid, propionic acid, butyric acid, valeric acid, caproic acid, heptanoic acid, caprylic acid, pelargonic acid, capric acid, undecanoic acid, lauric acid, tridecanoic acid, tetradecanoic acid, pentadecanoic acid, palmitic acid, margaric acid, stearic acid, nonadecanoic acid, arachidic acid, behenic acid, lignoceric acid, cerotic acid, melissic acid, isobutyric acid, isovaleric acid, tuberculostearic acid, acrylic acid, crotonic acid, palmitoleic acid, oleic acid, erucic acid, sorbic acid, linoleic acid, linolenic acid, eleostearic acid, arachidonic acid, clupanodonic acid, docosahexaenoic acid, oxalic acid, malonic acid, succinic acid, glutaric acid, adipic acid, pimelic acid, azelaic acid, sebacic acid, maleic acid, fumaric acid, muconic acid, phthalic acid, and terephthalic acid.

Especially preferred agents of the invention are characterized in that the chitosan derivative(s), present in them, is/are selected from
chitosan glycolate
N-acetyl-chitosan (chitosan acetate)
N-propionyl-chitosan (chitosan propionate)
N-butanoyl-chitosan (chitosan butanoate)
N-malonyl-chitosan (chitosan malonate)
N-succinyl-chitosan (chitosan succinate)
N-adipyl-chitosan (chitosan adipate).

The compositions of the invention include as the third essential ingredient, based on their weight, 1 to 20% by weight of precipitated silicic acid(s) with a specific surface of ≤60 m$^2$/g according to ISO 5794-1, Annex D. Preferably, the precipitated silicic acids, which have suitable specific surfaces, are used within rather narrow quantity ranges, and precipitated silicic acids that have even lower specific surfaces according to ISO 5794-1, Annex D, are used particularly preferably. Preferred oral and dental hygiene and cleaning agents of the invention include 2.5 to 19.5% by weight, preferably 5 to 19% by weight, especially preferably 7.5 to 18.5% by weight, more preferably 8.0 to 18% by weight, and in particular 10.0 to 17.5% by weight of precipitated silicic acid(s) with a specific surface of ≤55 m$^2$/g according to ISO 5794-1, Annex D.

Especially preferred oral and dental hygiene and cleaning agents of the invention are characterized in that all precipitated silicic acid(s), included in the agent, have a specific surface of ≤60 m$^2$/g, preferably of ≤52.5 m$^2$/g, more preferably of ≤49 m$^2$/g, and in particular of ≤47 m$^2$/g according to ISO 5794-1, Annex D.

In further preferred agents of the invention, the employed precipitated silicic acids are characterized by other physical parameters. Precipitated silicic acids that are to be used preferably have tamped densities >360 g/L (measured according to ISO 787-11), particularly preferably >375 g/L, more preferably >400 g/L, and in particular >425 g/L.

It is preferred further to use precipitated silicic acids that have a DBP absorption of less than 140 g/100 g according to DIN 53601. Very particularly preferred precipitated silicic acids to be used according to the invention have a DBP absorption according to DIN 53601 of less than 135 g/100 g, preferably a DBP absorption according to DIN 53601 of less than 130 g/100 g, and in particular of less than 125 g/100 g to.

Agents particularly preferred according to the invention include 2.5 to 25% by weight, preferably 5 to 20% by weight, particularly preferably 7.5 to 17.5% by weight, more preferably 8.0 to 15.0% by weight, and in particular 10.0 to 14.0% by weight of precipitated silicic acid(s) with a specific surface of ≤45 m²/g according to ISO 5794-1, Annex D, and a tamping density of >425 g/L (measured according to ISO 787-11).

Agents preferred further according to the invention include 2.5 to 25% by weight, preferably 5 to 20% by weight, particularly preferably 7.5 to 17.5% by weight, more preferably 8.0 to 15.0% by weight, and in particular 10.0 to 14.0% by weight of precipitated silicic acid(s) with a specific surface of ≤45 m²/g according to ISO 5794-1, Annex D, and a DBP absorption of less than 125 g/100 g according to DIN 53601.

Agents particularly preferred according to the invention include 2.5 to 25% by weight, preferably 5 to 20% by weight, particularly preferably 7.5 to 17.5% by weight, more preferably 8.0 to 15.0% by weight, and in particular 10.0 to 14.0% by weight of precipitated silicic acid(s) with a specific surface of ≤45 m²/g according to ISO 5794-1, Annex D, and a tamping density of >425 g/L (measured according to ISO 787-11), and a DBP absorption of less than 125 g/100 g according to DIN 53601.

The agents of the invention can include other polishing agents, in addition to the aforementioned precipitated silicic acids a). All friction bodies known for toothpastes are suitable in principle as polishing agents, particularly those that include no calcium ions. Preferably suitable polishing agent components therefore are aluminum hydroxide, aluminum oxide, sodium aluminum silicates, organic polymers, or mixtures of such friction bodies.

It is preferred that the compositions of the invention include only little to no precipitated silicic acids that have a specific surface of >55 m²/g according to ISO 5794-1, Annex D. If such silicic acids were to be used, the weight ratio of precipitated silicic acids with a specific surface of ≤55 m²/g according to ISO 5794-1, Annex D, (ingredient c)) to precipitated silicic acids with a specific surface according to ISO 5794-1, Annex D, of >55 m²/g is preferably >1:1, more preferably >2:1, even more preferably >5:1, particularly preferably >10:1, and in particular >50:1.

For example, aluminum oxide in the form of low-calcined alumina with a content of—and -aluminum oxide in an amount of about 1 to 5% by weight can also be included as further polishing agent components. Such a suitable aluminum oxide can be obtained under the trade name "ultrafine polishing alumina P 10" (Giulini Chemie). Suitable as polishing agents, further, are all friction bodies known for toothpastes such as e.g., sodium aluminum silicates such as, e.g., zeolite A, organic polymers such as, e.g., polymethacrylate or mixtures thereof, and the aforementioned friction bodies.

The agents of the invention can include as a further ingredient 0.001 to 10.0% by weight of at least one calcium salt. Used particularly preferably are calcium salt(s) within rather narrow quantity ranges, so that preferred oral and dental hygiene and cleaning agents include 0.05 to 7.5% by weight, preferably 0.1 to 5% by weight, more preferably 0.15 to 2.5% by weight, and in particular 0.2 to 1.25% by weight of calcium salt(s).

All physiologically acceptable calcium salts can be used according to the invention; the use of calcium salts is preferred that exhibit further benefits in the oral and dental hygiene and cleaning agents of the invention. Very especially preferred of these compounds are calcium hydrogen phosphate dihydrate and/or calcium glycerophosphate.

Calcium hydrogen phosphate dihydrate, $CaHPO_4 \cdot 2H_2O$, is also called "brushite" or dicalcium phosphate dihydrate depending on the literature reference. The use of $CaHPO_4 \cdot 2H_2O$ is preferred according to the invention, which is described by the CAS-No. 7789-77-7.

Oral and dental hygiene and cleaning agents of the invention, which include as the calcium salt calcium hydrogen phosphate dihydrate, $CaHPO_4 \cdot 2H_2O$, have pronounced abrasiveness advantages compared with other agents; the gentle cleaning of sensitive teeth is therefore even better with the combination of the invention of polylactic acid, defined silicate, and calcium hydrogen phosphate dihydrate as the calcium salt.

It turned out that calcium hydrogen phosphate dihydrate, $CaHPO_4 \cdot 2H_2O$, is used preferably within narrow quantity ranges. Oral and dental hygiene and cleaning agents of the invention are preferred here that include 0.25 to 7.5% by weight, preferably 0.5 to 7.0% by weight, particularly preferably 1.0 to 6.0% by weight, more preferably 2.0 to 5.0% by weight, and in particular 3.5 to 4.5% by weight of calcium hydrogen phosphate dihydrate.

In addition to calcium hydrogen phosphate dihydrate or instead of it, the agents of the invention can include with particular advantage calcium glycerophosphate, i.e., a calcium salt of at least one glycerophosphoric acid.

Glycerophosphoric acid is a dibasic acid, which occurs in two isomer forms, depending on whether the phosphoric acid group is bound to a terminal or medial OH group of glycerol. The form in which the phosphoric acid group is bound to a terminal OH group of glycerol is also called the alpha-isomer, and the form in which the phosphoric acid group is bound to the medial OH group of glycerol is also called the beta-isomer.

The alpha-isomer is optically active in addition and occurs in the two enantiomeric forms of sn-glycerol-1-phosphoric acid

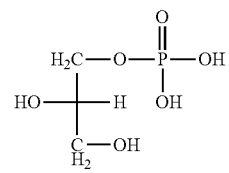

and sn-glycerol-3-phosphoric acid

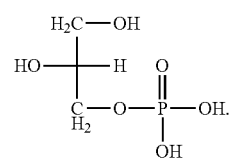

The prefix sn in glycerol derivatives stands for "stereospecifically numbered" and requires that the 2-hydroxy group points to the left in the Fischer projection used above. Glycerol-2-phosphate is not optically active. Glycerophosphoric acids are approximately as strong as phosphoric acid The use of the alpha-isomer is preferred according to the invention, regardless of which of the two enantiomers is used. Provided the use of enantiomerically pure compounds is desired, the calcium salt of sn-glycerol-3-phosphoric acid is used preferably.

In summary, oral and dental hygiene and cleaning agents of the invention are preferred that include the calcium salts of glycerophosphoric acid of formulas (Ia) and (Ib)

In this case, especially preferred oral and dental hygiene and cleaning agents of the invention are characterized in that the weight ratio of the calcium salts of formulas (Ia) to (Ib) is above 50:50, preferably above 60:40, particularly preferably above 70:30, and in particular above 80:20.

The use of the calcium glycerophosphates within rather narrow quantity ranges is preferred. Preferred oral and dental hygiene and cleaning agents of the invention include, based on their weight, 0.01 to 2.5% by weight, preferably 0.05 to 2.0% by weight, particularly preferably 0.1 to 1.0% by weight, more preferably 0.11 to 0.75% by weight, and in particular 0.12 to 0.5% by weight of calcium glycerophosphate.

Very especially preferred agents of the invention include 0.25 to 7.5% by weight, preferably 0.5 to 7.0% by weight, particularly preferably 1.0 to 6.0% by weight, more preferably 2.0 to 5.0% by weight, and in particular 3.5 to 4.5% by weight of calcium hydrogen phosphate dihydrate and 0.01 to 2.5% by weight, preferably 0.05 to 2.0% by weight, particularly preferably 0.1 to 1.0% by weight, more preferably 0.11 to 0.75% by weight, and in particular 0.12 to 0.5% by weight of calcium glycerophosphate.

Surface-active substances can also be used in the agents of the invention. They are used, for example, in toothpastes to support the cleaning action and if desired also to create foam during the brushing of teeth or in the rinsing of the mouth, as well as to stabilize the polishing substance dispersion in the carrier, and are used both in mouth rinse solutions and in toothpastes typically in an amount of 0.1 to 5% by weight.

Suitable surfactants are, e.g., linear sodium alkyl sulfates having 12-18 C atoms in the alkyl group. These substances have in addition an enzyme-inhibiting effect on bacterial metabolism in plaque. Other suitable surfactants are alkali salts, preferably sodium salts of alkyl polyglycol ether sulfate having 12-16 C atoms in the linear alkyl group and 2-6 glycol ether groups in the molecules, of linear alkane ($C_{12}$-$C_{18}$) sulfonate, of sulfosuccinic acid monoalkyl ($C_{12}$-$C_{18}$) esters, of sulfated fatty acid monoglycerides, sulfated fatty acid alkanolamides, sulfoacetic acid alkyl ($C_{12}$-$C_{16}$) esters, acylsarcosines, acyltaurides, and acylisothionates each having 8-18 C atoms in the acyl group. Zwitterionic, ampholytic, and nonionic surfactants are also suitable, e.g., ethoxylates of fatty acid mono- and diglycerides, of fatty acid sorbitan esters, and alkyl (oligo)glucosides and fatty acid amidoalkyl betaine.

It is preferred according to the invention to limit to a very great degree the use of surfactants in order to be able to allow the desensitizing effect of the combination of the invention to be even more prominent. Therefore, the oral and dental hygiene and cleaning agents of the invention are especially preferred according to the invention that, based on their weight, include less than 5% by weight, preferably less than 4% by weight, particularly preferably less than 3% by weight, and in particular less than 2% by weight of surfactant(s).

It is very especially preferred to limit to a very great degree the use of anionic surfactants or to dispense with these surfactants entirely. In this case, preferred oral and dental hygiene and cleaning agents of the invention are characterized in that they include less than 2% by weight, preferably less than 1% by weight, particularly preferably less than 0.5% by weight, and in particular less than 0.1% by weight of anionic surfactant(s), whereby preferred agents are free of anionic surfactants.

Provided surfactants are to be used preferably within the aforementioned maximum limits, the use of amphoteric surfactants is preferred. Preferred surfactant-containing oral and dental hygiene and cleaning agents of the invention include 0.1 to 5% by weight, preferably 0.25 to 4% by weight, particularly preferably 0.5 to 3.0% by weight, more preferably 0.75 to 2.0% by weight, and in particular 1.0 to 1.5% by weight of amphoteric surfactant(s).

Especially preferred oral and dental hygiene and cleaning agents of this embodiment according to the invention include 0.1 to 5% by weight, preferably 0.2 to 4% by weight, particularly preferably 0.25 to 3% by weight, more preferably 0.3 to 2% by weight, and in particular 0.4 to 0.8% by weight of cocamidopropyl betaine.

The oral and dental hygiene and cleaning agents of the invention may include other ingredients. Preferred in this case is the use of so-called humectants, which prevent the drying out of toothpaste. In so-called liquid dental creams with flowable rheology, they serve as a matrix and are used in higher amounts. In mouthwashes and mouth rinses, these alcohols function as consistency regulators and additional sweeteners.

Here, oral and dental hygiene and cleaning agents of the invention are preferred that include, based on their weight, 0.5 to 60% by weight, preferably 0.75 to 55% by weight, particularly preferably 1 to 50% by weight, and in particular 2 to 40% by weight of at least one polyhydric alcohol from the group comprising sorbitol and/or glycerol and/or 1,2-propylene glycol or mixtures thereof.

It can be advantageous for specific fields of application to use only one of the three aforementioned ingredients. Sorbitol is preferred in most cases. Nevertheless, mixtures of two of the three substances or all three substances can be preferred in other fields of application. A mixture of glycerol, sorbitol, and 1,2-propylene glycol in a weight ratio of 1:(0.5-1):(0.1-0.5) has proven especially advantageous here.

Apart from sorbitol or glycerol or 1,2-propylene glycol, alcohols with at least 2 OH groups, preferably mannitol, xylitol, polyethylene glycol, polypropylene glycol, and mixtures thereof, are suitable as other polyhydric alcohols. Of these compounds, those with 2 to 12 OH groups and particularly those with 2, 3, 4, 5, 6, or 10 OH groups are preferred.

Polyhydroxy compounds with 2 OH groups are, for example, glycol ($CH_2(OH)CH_2OH$) and other 1,2-diols such as H—$(CH_2)_n$—$CH(OH)CH_2OH$ with n=2, 3, 4, 5, 6, 7, 8, 9, 10, 11, 12, 13, 14, 15, 16, 17, 18, 19, 20. 1,3-Diols such as H—$(CH_2)_n$—$CH(OH)CH_2CH_2OH$ with n=1, 2, 3, 4, 5, 6, 7, 8, 9, 10, 11, 12, 13, 14, 15, 16, 17, 18, 19, 20 can also be used according to the invention. The (n,n+1) or (n,n+2) diols with non-terminal OH groups can also be used. Important representatives of polyhydroxy compounds with 2 OH groups are also polyethylene and polypropylene glycols. For example, xylitol, propylene glycols, polyethylene glycols, particularly those with average molecular weights of 200-800, can be used as preferred other polyhydric alcohols.

Especially preferred is the use of sorbitol, so that agents that include no polyhydric alcohols other than sorbitol are especially preferred.

The agents of the invention can also include in addition further wound-healing and anti-inflammatory substances, e.g., active substances against gum inflammation. Such substances can be selected, e.g., from allantoin, azulene, chamomile extracts, tocopherol, panthenol, bisabolol, and sage extracts.

Oral and dental hygiene and cleaning agents can also include, e.g., substances that are effective against plaque and/or tartar.

Substances effective against tartar can be chelating agents, for example, such as, e.g., ethylenediaminetetraacetic acid and sodium salts thereof, pyrophosphate salts such as the water-soluble dialkali or tetra-alkali metal pyrophosphate salts, e.g., $Na_4P_2O_7$, $K_4P_2O_7$, $Na_2K_2P_2O_7$, $Na_2H_2P_2O_7$, and $K_2H_2P_2O_7$ or polyphosphate salts, which can be selected, e.g., from water-soluble alkali metal tripolyphosphates such as sodium tripolyphosphate and potassium tripolyphosphate.

Oral and dental hygiene and cleaning agents preferred according to the invention are characterized in that they include in addition phosphate(s), preferably alkali metal phosphate(s), and particularly sodium tripolyphosphate, preferably in amounts of 1 to 10% by weight, particularly preferably of 2 to 8% by weight, and in particular of 3 to 7% by weight, in each case based on the entire agent.

Used as consistency regulators (or binders) are, e.g., natural and/or synthetic water-soluble polymers such as alginates, carrageenates, tragacanth, starch and starch ethers, cellulose ethers such as, e.g., carboxymethyl cellulose (Na salt), hydroxyethyl cellulose, methylhydroxypropyl cellulose, guar, acacia gum, agar-agar, xanthan gum, succinoglycan gum, locust bean gum, pectins, water-soluble carboxyvinyl polymers (e.g., Carbopol® types), polyvinyl alcohol, polyvinylpyrrolidone, and polyethylene glycols, particularly those with molecular weights of 1,500 to 1,000,000.

Other substances suitable for viscosity control are, e.g., phyllosilicates such as, e.g., montmorillonite clays, colloidal thickening silicic acids such as, e.g., aerogel silicic acid, pyrogenic silicic acid, or very finely ground precipitated silicic acids. Viscosity-stabilizing additives from the group of cationic, zwitterionic, or ampholytic nitrogen-containing surfactants, hydroxypropyl-substituted hydrocolloids, or polyethylene glycol/polypropylene glycol copolymers with an average molecular weight of 1000 to 5000 or a combination of the aforementioned compounds can also be used in toothpastes.

Xanthan gum is especially highly compatible with the combination of the invention. Agents of the invention, containing xanthan gum, are exceptionally storage-stable and have a pleasant product feel. Preferred oral and dental hygiene and cleaning agents of the invention are therefore characterized in that they include in addition 0.1 to 7.5% by weight, preferably 0.25 to 5% by weight, more preferably 0.5 to 2.5% by weight, and in particular 0.6 to 1.5% by weight of xanthan gum.

Apart from the aforementioned obligatory components, the dental hygiene agents of the invention can include other adjuvants and additives known per se. In this regard, an additive, which has been long known as a toothpaste component, is especially effective in the dental hygiene agent of the invention: calcium glycerophosphate, the calcium salt of glycero-1-phosphoric acid or glycero-2-phosphoric acid or glycero-3-phosphoric acid, which is an enantiomer of glycerol-1-phosphoric acid, or a mixture of said acids. The compound has a remineralizing action in dental hygiene agents, because it supplies both calcium ions and phosphate ions. Calcium glycerophosphate is used preferably in amounts of 0.01 to 1% by weight in the dental hygiene agents of the invention. Overall, the dental cleaning agents of the invention can include conventional adjuvants and additives in amounts up to 10% by weight.

The organoleptic properties of the dental hygiene agents of the invention can be improved, e.g., by the addition of aromatic oils and sweeteners.

All natural and synthetic fragrances, typical for oral and dental hygiene agents, can be used as aromatic oils. Natural fragrances can be included both in the form of natural essential oils, isolated from the crude material, and the individual components isolated therefrom.

Suitable fragrances are, e.g., peppermint oil, curled mint oil, *eucalyptus* oil, anise oil, fennel oil, caraway oil, menthyl acetate, cinnamaldehyde, anethole, vanillin, thymol, and mixtures of said components.

Suitable sweeteners are, e.g., sodium saccharin, sodium cyclamate, sucrose, lactose, maltose, and fructose.

Other conventional adjuvants and additives for toothpastes and mouthwashes or mouth rinse solutions are
- surface-active substances, preferably anionic, zwitterionic, amphoteric, nonionic surfactants or a combination of several different surfactants
- solvents and solubilizers, e.g., low monohydric or polyhydric alcohols or ethers, e.g., ethanol, 1,2-propylene glycol, diethylene glycol, or butyl diglycol
- pigments such as, e.g., titanium dioxide
- dyes
- buffer substances, e.g., primary, secondary, or tertiary alkali phosphates or citric acid/Na citrate
- other wound-healing or anti-inflammatory substances, e.g., allantoin, urea, azulene, chamomile active substances, acetylsalicylic acid derivatives, or rhodanide
- other vitamins such as, e.g., ascorbic acid, biotin, tocopherol, or rutin
- mineral salts such as, e.g., manganese, zinc, or magnesium salts.

The agents of the invention can be formulated as toothpastes or dental creams. A further subject of the present invention is the use of the agents of the invention for cleaning teeth by means of manual or electric toothbrushes. In the case of electrical toothbrushes, the agents of the invention have the further advantage that they are effective even in small amounts and, moreover, do not adversely affect the mechanics of the electrical brush head.

A further subject of the present invention is a method for cleaning teeth, characterized in that an agent of the invention is applied to the brush head of an electric toothbrush and the teeth are cleaned with the electric toothbrush.

A further subject of the present invention is a method for cleaning teeth, characterized by the steps
  a) providing a toothbrush whose brush head can be set in motion electrically,
  b) applying 0.5 to 5 g of an agent of the invention to the brush head,
  c) brushing the teeth for 30 to 300 seconds with the agent of the invention with use of the brush head set in motion electrically.

The statements made regarding the agents of the invention apply mutatis mutandis with respect to the preferred embodiments of the method of the invention.

The restaining of teeth can be effectively prevented by the use of the agents of the invention with polylactic particles. Another subject of the present invention, therefore, is a method for reducing discolorations on the tooth surface, in which method an oral and dental hygiene and cleaning agent is applied to the tooth surfaces, said agent including, based on its weight, a) 0.001 to 5% by weight of copolymer(s), comprising at least one structural unit of formula (A1) and at least one structural unit of formula (A2)

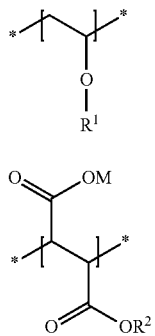

(A1)

(A2)

where $R^1$ stands for a ($C_1$ to $C_{18}$) alkyl group, $R^2$ stands for a ($C_1$ to $C_6$) alkyl group, M stands for a hydrogen atom or an equivalent of a mono- or polyvalent cation, b) 0.001 to 5% by weight of polymer(s) from the group comprising chitosan and chitosan derivatives, c) 1 to 20% by weight of precipitated silicic acid(s) with a specific surface of ≤60 m²/g according to ISO 5794-1, Annex D.

The statements made regarding the agents of the invention also apply mutatis mutandis with respect to preferred embodiments of said method of the invention.

EXAMPLES

All quantities are given in % by weight.

Example 1

Toothpaste Formulation

|  | A | B | C | D | E | F |
|---|---|---|---|---|---|---|
| Sorbitol, 70% | 45 | 50 | 55 | 60 | 65 | 70 |
| Copolymer* | 0.5 | 0.2 | 0.15 | 0.1 | 0.01 | 0.001 |
| Chitosan | 0.25 | 0.2 | 0.1 | 0.15 | 0.01 | 0.001 |
| Hydrated silica** | 20 | 18 | 17 | 15 | 12.5 | 15 |
| Sodium fluoride | 0.32 | 0.32 | 0.32 | 0.32 | 0.32 | 0.32 |
| Sodium saccharin | 0.25 | 0.25 | 0.25 | 0.25 | 0.25 | 0.25 |
| Ethanol | — | — | — | 1 | 2 | — |
| Xanthan | 0.2 | 0.1 | 0.3 | 0.2 | 0.2 | 0.1 |
| Sodium lauryl ether sulfate | 1.2 | 1.2 | 1.2 | 1.2 | 1.2 | 1.2 |
| Cocamidopropyl betaine | 0.6 | 0.6 | 0.6 | 0.6 | 0.6 | 0.6 |
| Aroma | 0.1 | 0.1 | 0.1 | 0.1 | 0.1 | 0.1 |
| Water | To 100 | | | | | |

*Copolymer of maleic acid and methyl vinyl ether, MW 1,200,000 daltons
**Precipitated silicic acid(s) with a specific surface of ≤45 m²/g according to ISO 5794-1, Annex D Example 2

Mouthwash Formulation

|  | A | B | C | D | E | F |
|---|---|---|---|---|---|---|
| Sorbitol, 70% | 1 | 1.5 | 2 | 2.5 | 3 | 5 |
| Copolymer* | 0.5 | 0.2 | 0.15 | 0.1 | 0.01 | 0.001 |
| Chitosan | 0.25 | 0.2 | 0.1 | 0.15 | 0.01 | 0.001 |
| Hydrated silica** | 1 | 1.5 | 2 | 2.5 | 1 | 1 |
| Sodium fluoride | 0.11 | 0.11 | 0.11 | 0.11 | 0.11 | 0.11 |
| Sodium saccharin | 0.03 | 0.05 | 0.1 | 0.05 | 0.05 | 0.1 |
| PEG-60 Hydrogenated castor oil | 0.2 | 0.2 | 0.2 | 0.2 | 0.2 | 0.2 |
| Trisodium citrate dihydrate | 0.1 | 0.2 | 0.3 | 0.2 | 0.1 | 0.1 |
| Citric acid | 0.001 | 0.002 | 0.1 | 0.2 | 0.01 | 0.01 |
| Cetylpyridinium chloride | 0.01 | 0.1 | 0.05 | 0.05 | 0.1 | 0.01 |
| Aroma | | | | | | |
| Water | To 100 | | | | | |

Evidence of Effectiveness:

Tooth models were treated with the formulations F-E (according to the invention) and F-V1 (chitosan only) or F-V2 (copolymer only), whereby the compositions were applied in an identical amount and manner. The pretreated tooth models were then stored at 20° C. for 7 hours in brewed black tea and the change in color was measured.

|  | F-E | F-V1 | F-V2 |
|---|---|---|---|
| Sorbitol, 70% | 70 | 70 | 70 |
| Copolymer* | 0.001 | — | 0.002 |
| Chitosan | 0.001 | 0.002 | — |
| Hydrated silica** | 15 | 15 | 15 |
| Sodium fluoride | 0.32 | 0.32 | 0.32 |
| Sodium saccharin | 0.25 | 0.25 | 0.25 |
| Ethanol | — | — | — |
| Xanthan gum | 0.1 | 0.1 | 0.1 |
| Sodium lauryl ether sulfate | 1.2 | 1.2 | 1.2 |
| Cocamidopropyl betaine | 0.6 | 0.6 | 0.6 |
| Aroma | 0.1 | 0.1 | 0.1 |
| Water | To 100 | | |

The following table shows the Delta E values of the tea stain after 7 h on the pretreated tooth models:

|  | F-E | F-V1 | F-V2 |
|---|---|---|---|
| Delta E | 27.2 | 35.5 | 33.7 |

The results clearly show that the restaining is the lowest with the composition of the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oral and dental hygiene and cleaning agent, including, based on its weight,
   a) 0.001 to 5% by weight of copolymer(s), comprising at least one structural unit of formula (A1) and at least one structural unit of formula (A2)

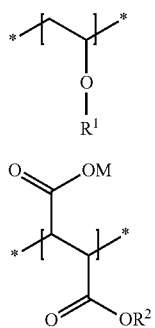

where
R$^1$ stands for a (C$_1$ to C$_{18}$) alkyl group,
R$^2$ stands for a (C$_1$ to C$_6$) alkyl group,
M stands for a hydrogen atom or an equivalent of a mono- or polyvalent cation;
   b) 0.001 to 5% by weight of polymer(s) from the group comprising chitosan and chitosan derivatives,
   c) 1 to 20% by weight of precipitated silicic acid(s) with a specific surface of ≤60 m$^2$/g according to ISO 5794-1, Annex D.

2. The oral and dental hygiene and cleaning agent according to claim 1, wherein the copolymer is present in an amount of 0.002 to 4% by weight based on the total weight of the agent.

3. The oral and dental hygiene and cleaning agent according to claim 1, wherein the copolymer is present in an amount of 0.005 to 1% by weight based on the total weight of the agent.

4. The oral and dental hygiene and cleaning agent according to claim 1, wherein the copolymer(s), comprising at least one structural unit of the formula (A1) and at least one structural unit of the formula (A2), has a molar mass of 500,000 to 5,000,000 daltons.

5. The oral and dental hygiene and cleaning agent according to claim 1, wherein the copolymer(s), comprising at least one structural unit of the formula (A1) and at least one structural unit of the formula (A2), has a molar mass of 900,000 to 1,500,000 daltons.

6. The oral and dental hygiene and cleaning agent according to claim 1, wherein the polymer selected from chitosan and chitosan derivatives is present in an amount of 0.002 to 4% by weight, based on the total weight of the agent.

7. The oral and dental hygiene and cleaning agent according to claim 1, wherein the polymer selected from chitosan and chitosan derivatives is present in an amount of 0.005 to 1% by weight, based on the total weight of the agent.

8. The oral and dental hygiene and cleaning agent according to claim 1, wherein the silicic acid(s) with a specific surface of ≤55 m$^2$/g according to ISO 5794-1, Annex D is present in an amount of 2.5 to 19.5% by weight, based on the total weight of the agent.

9. The oral and dental hygiene and cleaning agent according to claim 1, wherein the silicic acid(s) with a specific surface of ≤55 m$^2$/g according to ISO 5794-1, Annex D is present in an amount of 8.0 to 18% by weight, based on the total weight of the agent.

10. The oral and dental hygiene and cleaning agent according to claim 1, wherein the precipitated silicic acid(s), included in the agent, have a specific surface according to ISO 5794-1, Annex D, of ≤60 m$^2$/g.

11. The oral and dental hygiene and cleaning agent according to claim 1, wherein the precipitated silicic acid(s), included in the agent, have a specific surface according to ISO 5794-1, Annex D, of ≤52.5 m$^2$/g.

12. The oral and dental hygiene and cleaning agent according to claim 1, wherein the precipitated silicic acid(s), included in the agent, have a specific surface according to ISO 5794-1, Annex D, of ≤49 m$^2$/g.

13. The oral and dental hygiene and cleaning agent according to claim 1, wherein all of the precipitated silicic acid(s), included in the agent, have a specific surface according to ISO 5794-1, Annex D, of ≤60 m$^2$/g.

14. The oral and dental hygiene and cleaning agent according to claim 1, wherein all the precipitated silicic acid(s), included in the agent, have a specific surface according to ISO 5794-1, Annex D, of ≤52.5 m$^2$/g.

15. The oral and dental hygiene and cleaning agent according to claim 1, wherein all the precipitated silicic acid(s), included in the agent, have a specific surface according to ISO 5794-1, Annex D, of ≤49 m$^2$/g.

16. The oral and dental hygiene and cleaning agent according to claim 1, further comprising 0.01 to 2.5% by weight calcium glycerophosphate, based on the total weight of the agent.

17. The oral and dental hygiene and cleaning agent according to claim 1, further comprising 0.11 to 0.75% by weight calcium glycerophosphate, based on the total weight of the agent.

18. The oral and dental hygiene and cleaning agent according to one of claim 1, wherein the agent includes less than 5% by weight of surfactants.

19. The oral and dental hygiene and cleaning agent according to one of claim 1, wherein the agent includes less than 2% by weight of surfactants.

20. A method for the cleaning of teeth, characterized by the steps
   a) providing a toothbrush whose brush head can be set in motion electrically,
   b) applying 0.5 to 5 g of an agent according to claim 1 to the brush head,
   c) brushing the teeth for 30 to 300 seconds with the agent.

* * * * *